(12) United States Patent
Bhatnagar et al.

(10) Patent No.: US 6,509,318 B1
(45) Date of Patent: Jan. 21, 2003

(54) TGF-B INHIBITORS AND METHODS

(75) Inventors: Rajendra S. Bhatnagar, Burlingame, CA (US); Craig A. Gough, Daly City, CA (US); Jing Jing Qian, Foster City, CA (US)

(73) Assignee: The Regents of the University of California, Oakland, CA (US)

( * ) Notice: Subject to any disclaimer, the term of this patent is extended or adjusted under 35 U.S.C. 154(b) by 109 days.

(21) Appl. No.: 09/676,108

(22) Filed: Sep. 29, 2000

(51) Int. Cl.$^7$ .................. A61K 38/03; A61K 38/08; C07K 7/06
(52) U.S. Cl. .................. 514/17; 530/329; 530/399
(58) Field of Search .................. 514/2, 17; 530/329, 530/399

(56) References Cited

U.S. PATENT DOCUMENTS

| | | | |
|---|---|---|---|
| 5,662,904 A | 9/1997 | Ferguson et al. | 424/130.1 |
| 5,780,436 A | * 7/1998 | Bhatnager et al. | 514/18 |
| 5,958,411 A | 9/1999 | Logan et al. | 424/158.1 |
| 5,972,335 A | 10/1999 | Ferguson et al. | 424/141.1 |
| 6,062,460 A | 5/2000 | Sato | 228/119 |

FOREIGN PATENT DOCUMENTS

WO   WO 98/18816   5/1998

OTHER PUBLICATIONS

Henry (2000) "Special Delivery: Alternative methods for delivering drugs improve performance, convenience, and patient compliance." *C &EN*, p. 49–65.

\* cited by examiner

*Primary Examiner*—Christopher S. F. Low
*Assistant Examiner*—Anish Gupta
(74) *Attorney, Agent, or Firm*—Bozicevic, Field & Francis LLP; Carol L. Francis

(57) ABSTRACT

A family of small peptides have been found to be inhibitory to TGF-β activity, and preferably have the primary structure of Formula I:

$AA_1$-$AA_2$-$AA_3$-Pro-D-Glu-Ala         FORMULA I wherein $AA_1$ is leucine, phenylalanine, α-aminoisobutric acid, N-methylalanine, N-methylisoleucine, or isoleucine; $AA_2$ is the same or a different amino acid residue as in $AA_1$; and $AA_3$ is alanine or N-methylalanine.

16 Claims, No Drawings

TGF-β INHIBITORS AND METHODS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention generally relates to agents that inhibit the activity of TGF-β for uses such as scar tissue inhibition during wound healing, and more particularly to small peptides with potent anti-transforming growth factor β activity and useful in countering the effect of increased TGF-β activity seen in many pathological conditions.

2. Description of Related Art

Increased levels of transforming growth factor β (TGF-β) activity are involved in a large number of pathologic conditions, including, but not limited to, the following: (i) fibrosis, scarring, and adhesion during wound healing; (ii) fibrotic diseases of the lungs, liver, kidneys; (iii) atherosclerosis and arteriosclerosis; (iv) certain types of cancer including cancer of the prostate, neuroendocrine tumors of the digestive system, cancer of the cervix, glioblastomas, and gastric cancer; (v) angiopathy, vasculopathy, nephropathy; (vi) systemic sclerosis; (vii) viral infection such as hepatitis C and HIV; and (viii) immunological disorders and deficiencies.

For example, members of the TGF-β family are among the peptides known to have a number of biological activities related to tumorigenesis (including angiogenesis) and metastasis. TGF-β inhibits the proliferation of many cell types including capillary endothelial cells and smooth muscle cells. TGFβ downregulates integrin expression ($\alpha 1\beta 1$, $\alpha 2\beta 1$, $\alpha v\beta 3$ involved in endothelial cell migration). Integrins are involved in the migration of all cells, including metastatic ones. TGF-β downregulates matrix metalloproteinase expression needed for both angiogenesis and metastasis. TGF-β induces plasminogen activator inhibitor, which inhibits a proteinase cascade needed for angiogenesis and metastasis. TGF-β induces normal cells to inhibit transformed cells.

Transforming growth factor-βs were originally named for their ability to transform normal fibroblasts to cells capable of anchorage-independent growth. The effects of TGF-βs on cells are generally classified as proliferative and non-proliferative. As originally established with the first experiments on fibroblasts, TGF-βs are bona fide growth factors. Two important cell types in which proliferation is enhanced by TGF-β are osteoblasts and Schwann cells of the peripheral nervous system. However, in many cells, TGF-βs are potent inhibitors of cell proliferation. This negative growth control may be the regulatory mechanism that checks regeneration of certain tissues and may play a role in the initiation of carcinogenesis.

The most important non-proliferative function of TGF-βs are in enhancing the formation of extracellular matrices. Although this is achieved primarily through the increased transcription of both collagen and fibronectin, the inhibition of the proteases from degrading the matrix also contributes to its stability. Degradation of the extracellular matrix is inhibited by the decrease in the secretion of the proteases themselves and the simultaneous increase in the levels of protease inhibitors.

Because of the wide applicability of TGF-βs in clinical therapies, they have been the focus of much research. Although much of the research involved in vitro uses, recent in vivo studies have confirmed some of the more promising in vitro effects.

The natural members of the transforming growth factor-β family range upwards of 25 KDa molecular weight. Clinical uses of growth factors, including TGF-βs, may be limited because of their size, which can cause immune responses. For example, human TGF β-1 is a 25,000 dalton homodimeric protein. In addition to possible adverse immunological responses, large proteins are not often the best candidates for drugs because of the difficulties in administration and delivery.

Because of the involvement of TGF-β in a large number of serious pathological conditions, there is considerable interest in developing inhibitors of TGF-β. Many of the proposals for TGF-β inhibitors have involved antibodies.

For example, U.S. Pat. No. 5,662,904, issued Sep. 2, 1997, inventors Ferguson et al., describe a composition for use in treating wounds to inhibit scar tissue formation. An exemplary such composition has growth factor neutralizing antibody, such as antibodies to TGF β-1, TGF β-2, and PDGF.

U.S. Pat. No. 5,972,335, issued Oct. 26, 1999, inventors Ferguson et al., disclose compositions comprising at least two antibodies for use in promoting wound healing or fibrotic disorders, where the first antibody is specific for a single epitope on TGF β-1 and the second antibody is specific for a single epitope on TGF β-2.

U.S. Pat. No. 6,062,460, issued May 9, 2000, inventor Ferguson, discloses the use of soluble betaglycan (otherwise known as TGF-β receptor III) for use in promoting wound healing of fibrotic disorders with reduced scarring.

U.S. Pat. No. 5,958,411, issued Sep. 28, 1999, inventors Logan and Baird, disclose methods for treating a CNS pathology by administering neutralizing anti-TGF-β antibodies.

However, antibodies and receptors are large proteins. Because of the amounts of TGF β-1 in serum of subjects with diseases such as prostate cancer (which are as high as 35 ng/ml), very large quantities of "neutralizing" proteins, such as antibodies, would need to be administered. This poses a difficult problem and adverse effects can be anticipated. Furthermore, while the amount of growth factor in the extracellular fluid is constantly increasing because of secretion from diseased cells, the number of cells and receptors is not likely to increase at the same rate. Therefore, a method that would target the receptor should mean that smaller amounts of a receptor inhibitor can be administered.

BRIEF SUMMARY OF THE INVENTION

In one aspect of the present invention, a family of small peptides have been found to be inhibitory to TGF β-1 and which preferably have the primary structure of Formula I.

$$AA_1\text{-}AA_2\text{-}AA_3\text{-}Pro\text{-}D\text{-}Glu\text{-}Ala \qquad \text{FORMULA I}$$

The N-terminal amino acid residue designated $AA_1$ may include a blocking group, for example may be acylated, and preferably is leucine, phenylalanine, α-aminoisobutric acid (Aib), N-methylalanine (NmeA), N-methylisoleucine, or isoleucine; $AA_2$ is the same or a different amino acid residue as described for AA₁; and AA₃ is alanine or N-methylalanine. The C-terminal alanine may also include a blocking group, for example, may be amidated or esterified. Three particularly preferred such inhibitors are Glu-Ile-Ala-Pro-D-Glu-Ala (sometimes hereinafter "CITA-I"), Phe-Ile-Ala-Pro-D-Glu-Ala ("CITA-II"), and Leu-Phe-Ala-Pro-D-Glu-Ala ("CITA-III"). These three particularly preferred embodiments markedly reverse the inhibition of DNA synthesis caused by TGF β-1.

Because the TGF-β inhibitors of the present invention are small peptides, they are easily synthesized, obtained in highly pure form, and can be readily delivered in a wide variety of modalities. For example, the Formula I peptides may be applied topically to wounds so as to prevent adhesions and scarring, they may be delivered by injection to affect the behavior of tumors, fibrotic tissues, sites of inflammation, and to modulate the behavior of cells of the immune system.

DETAILED DESCRIPTION OF THE INVENTION

In our copending application Ser. No. 09/113,696, filed Jul. 10, 1998, inventors Bhatnagar, Qian, and Gough, of common assignment herewith, we describe a series of small peptides we called "cytomodulin analogs" which were found active as TGF-β agonists. One of these was L-I-A-P-(D-Glu)-A. These cytomodulin analogs were suggested as having utility in surgery as agents which promote wound healing and regeneration.

In the subject application, the earlier L-I-A-P-(D-Glu)-A, which we had studied for its activity as a TGF-β agonist, together with now other, novel compounds have been found to be inhibitory to TGF-β activity. We have designated them by the acronym "CITA." These CITA compounds are preferably hexapeptides having the primary structure of Formula I.

AA₁-AA₂-AA₃-Pro-D-Glu-Ala            FORMULA I wherein AA₁ is an amino acid residue from the group of leucine, phenylalanine, α-aminoisobutric acid (Aib), N-methylalanine (NmeA), N-methylisoleucine, and isoleucine; AA₂ is the same or a different amino acid residue as described for AA₁; and AA₃ is alanine or N-methylalanine.

Thus, our earlier described L-I-A-P-(D-Glu)-A (Leu-Ile-Ala-Pro-D-Glu-Ala) is one of the preferred CITA, Formula I embodiments. Another two particularly preferred embodiments are Phe-Ile-Ala-Pro-D-Glu-Ala and Leu-Phe-Ala-Pro-D-Glu-Ala, sometimes hereinafter designated "CITA-II" and "CITA-III," respectively.

The AA₁ and AA₂ amino acid residues of Formula I constitute large, hydrophobic side chains. It is believed that the hydrophobic side chains of AA₁ and AA₂ occupy the large hydrophobic pocket in the receptor, and can move freely and interact with several portions of the pocket. The presence of the proline in the four position and D-Glu residue in the five position are believed to constrain the conformation.

The surprising antagonistic nature of the CITA peptides with their D-Glu containing amino acid residues is likely due to the inability of these peptides to undergo a conformational change necessary for signaling activity after they bind to the TGF β-1 receptor. Although their side-chain functional groups can adopt the correct relative positions and orientations to allow favorable interactions with the complementary receptor functional groups, the conformational constraints probably do not allow the peptide-receptor complex to undergo the required change in conformation. This may be partially due to the rigidity of the proline and the induced rigidity of the alanine on its N-terminal side, but since some proline and hydroxyproline peptides are agonists, the D-Glu residue appears to play the major role.

Although D-Glu can place its carbonyl oxygens in the correct positions for receptor binding, its intrinsic backbone conformational tendencies are quite different from L-Glu; a D-amino acid's Φ, Ψ conformational energy map is approximately a mirror image of the corresponding L-amino acid, with the mirror plane running from the upper left corner to the lower right corner.

Peptides of the present invention can be synthesized by various suitable methods that are well known in the art, preferably by solid phase synthesis, manual or automated, as first developed by Merrifield and described by Stewart et al. in *Solid Phase Peptide Synthesis* (1984). Chemical synthesis joins the amino acids in the predetermined sequence starting at the C-terminus. Basic solid phase methods require coupling the C-terminal protected α-amino acid to a suitable insoluble resin support. Amino acids for synthesis require protection on the α-amino group to ensure proper peptide bond formation with the preceding residue (or resin support). Following completion of the condensation reaction at the carboxyl end, the α-amino protecting group is removed to allow the addition of the next residue. Several classes of α-protecting groups have been described, see Stewart et al. in *Solid Phase Peptide Syntiesis* (1984), with the acid labile, urethan-based tertiary-butyloxycarbonyl (Boc) being the historically preferred. Other protecting groups, and the related chemical strategies, may be used, including the base labile 9-fluorenylmethyloxycarbonyl (FMOC). Also, the reactive amino acid sidechain functional groups require blocking until the synthesis is completed. The complex array of functional blocking groups, along with strategies and limitations to their use, have been reviewed by Bodansky in *Peptide Sythesis* (1976) and, Stewart et al. in *Solid Phase Peptide Synthesis* (1984).

Solid phase synthesis is initiated by the coupling of the described C-terminal α-protected amino acid residue. Coupling requires activating agents, such as dicyclohexycarbodiimide (DCC) with or without 1-hydroxybenzo-triazole (HOBT), diisopropylcarbodiimide (DIIPC), or ethyldimethylaminopropylcarbodiimide (EDC). After coupling the C-terminal residue, the α-amino protected group is removed by trifluoroacetic acid (25% or greater) in dichloromethane in the case of acid labile tertiary-butyloxycarbonyl (Boc) groups. A neutralizing step with triethylamine (10%) in dichloromethane recovers the free amine (versus the salt). After the C-terminal residue is added to the resin, the cycle of deprotection, neutralization and coupling, with intermediate wash steps, is repeated in order to extend the protected peptide chain. Each protected amino acid is introduced in excess (three to five fold) with equimolar amounts of coupling reagent in suitable solvent. Finally, after the completely blocked peptide is assembled on the resin support, reagents are applied to cleave the peptide form the resin and to remove the side chain blocking groups. Anhydrous hydrogen fluoride (HF) cleaves the acid labile tertiary-butyloxycarbonyl (Boc) chemistry groups. Several nucleophilic scavengers, such as dimethylsulfide and anisole, are included to avoid side reactions especially on side chain functional groups.

Modifications can be made to confer resistance to enzymatic degradation such as adding blocking groups to both the N- and C-terminal residues. Another method for preventing degradation and premature clearance by the renal system is the use of unnatural amino acid substitutes, such as Aib and NmeA, which may be in one or both of $AA_1$ and $AA_2$ positions.

Therapeutic compositions of this invention will be formulated depending upon the effective doses required and the modes of administration used. For example, pharmaceutical compositions can be formulated where the TGF-β inhibitor is in an amount of from 1 µg/kg to 10 mg/kg of patient weight. As a general proposition, the total pharmaceutically effective amount of each peptide administered will be subject to a great deal of therapeutic discretion.

The composition embodiments as therapeutic agents are administered to the patient by any suitable technique. The compositions to be used in the inventive therapy will be formulated and dosed in a fashion consistent with good medical practice, taking into account the clinical condition of the individual patient, the method of administration, the scheduling of administration, and other facts known to practitioners. The "effective amount" for purposes described herein is thus determined by such considerations.

We believe that these potent TGF β-1 antagonists will be useful in the treatment of a wide range of diseases where increased levels of TGF β-1 activity are implicated, including fibrosis, cancer, auto-immune disease, and a variety of viral infections accompanied by suppressed immune response. Each of these different applications will have preferred techniques for administration. A number of new methods for delivering drugs, including small peptides as here, are emerging to complement and expand traditional methods of drug delivery. For example, a review article published Sep. 18, 2000, in *C&EN*, pages 49–65, describes alternative methods for delivery drugs, such as pulmonary (inhalation) and oral formulations, as well as transdermal and extended-release injectable formulations.

Particularly contemplated for practicing this invention are tropical and systemic administrations, intravenous administration, subcutaneous administration, intraperitoneal injection, sub-periosteal injection, intra-tracheal administration, release from polymers or pumps, implants, or release from liposomes. Suitable implants (if using an implanted device) include, for example, gel foam, wax, or microparticle-based implants. For just one example, microsphere delivery technology are being adapted for injectable sustained release of drugs where peptides can be dispersed throughout microspheres. Doses used should be sufficient to achieve circulating plasma concentrations of active ingredient that are efficacious. Effective doses may be extrapolated from dose-response curves derived from in vitro or animal model test systems.

When the peptides are prepared for administration by mixing with physiologically acceptable carriers, i.e., carriers which are non-toxic to recipients at the dosages and concentrations employed, this will normally entail combining the inventive peptide(s) with buffers, antioxidants such as ascorbic acid, low molecular weight (less than about 10 residues) polypeptides, proteins, amino acids, carbohydrates including glucose or dextrins, chelating agents such as EDTA, and other excipients. When used in therapeutic administrations, the components must be sterile. This is readily accomplished by filtration through sterile filtration (0.22 micron) membranes.

The peptides may be administered in any pharmacologically acceptable carrier, and depending upon the desired mode of administration, may be formulated along with liquid carrier into liposomes, microcapsules, polymers or wax-based and controlled release preparations, or be formulated into tablet, pill, or capsule forms.

The peptides form pharmaceutically acceptable salts with organic and inorganic acids and can be administered in salt form and/or can be amidated. Examples of suitable acids for the formation of pharmaceutically acceptable salts are hydrochloric, sulfuric, phosphoric, acetic, benzoic, citric, malonic, salicylic, malic, fumaric, succinic, tartaric, lactic, gluconic, ascorbic, maleic, benzene-sulfonic, methane- and ethanesulfonic, hydroxymethane- and hydroxyethanesulfonic.

Salts may also be formed with suitable organic pharmaceutically acceptable base addition salts. These organic bases form a class whose limits are readily understood by those skilled in the art. Merely for purposes of illustration, the class may be said to include mono-, di-, and trialkylamines, such as methylamine, dimethylamine, and triethylamine; mono-, di-, or trihydroxyalkylamines such as mono-, di-, and triethanolamine; amino acids such as arginine, and lysine; guanidine; N-methyl-glucosamine; N-methylglucamine; L-glutamine; N-methylpiperazine; morpholine; ethylenediamine; N-benzylphenethylamine; tris(hydroxymethyl)aminomethane; and the like. (See, for example, "Pharmaceutical Salts," *J. Pharm. Sci.*, 66(1), 1–19 (1977).)

Therapeutic formulations containing at least one of the peptides may be prepared for storage by mixing with optional physiologically acceptable carriers, excipients or stabilizers, in the form of lyophilized cake or aqueous solutions. Acceptable carriers, excipients or stabilizers are nontoxic to recipients at the dosages and concentrations employed when administered, and include buffers such as phosphate, citrate, and other organic acids; antioxidants including ascorbic acid; low molecular weight (less than about 10 residues) polypeptides; proteins, such as serum albumin, gelatin or immunoglobulins.

Other components can include glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, PLURONICS or PEG.

Compositions may be used in the form of a sterile irrigant, preferably in combination with a physiological saline solution. Compositions for systemic administration preferably are formulated as sterile, isotonic parenteral injections or infusions.

Therapeutic compositions are typically prepared as liquid solutions or suspensions, or in solid forms. Formulations for wound healing usually will include such normally employed additives such as binders, fillers, carriers, preservatives, stabilizing agents, emulsifiers, buffers, and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%. Additional formulations which are suitable for other modes of administration, such as topical administration, include salves, tinctures, creams, lotions, and, in some cases, suppositories. For salves and creams, traditional binders, carriers, and excipients may include, for example, polyalkylene glycols or triglycerides.

The following examples are meant to illustrate but not limit the subject invention.

EXPERIMENTAL

Inhibition of TGF β-1 Activity by CITAs: We have used a standardized in vitro assay for TGF β-1 as a test for the biological activity of CITAs. Our test is based on inhibiting the effect of TGF β-1 on a test cell proliferation system. In this assay, mink lung epithelium MV-1-Lu cells are exposed to TGF β-1. This results in the inhibition of MV-1-Lu cells as seen in decreased DNA synthesis. The decrease in DNA synthesis can be monitored by measuring the incorporation of labeled precursors in DNA. The incorporation of $^3$H-thymidine in DNA in MV-1-Lu cells are used as a measure of cell proliferation. MV-1-Lu cells were exposed to two different concentrations of TGF β-1, 5.0 nM which decreased DNA synthesis by approximately 70%, and 10 nM which caused nearly a 97% inhibition respectively in the present experiments. These concentrations of TGF β-1 were based on the amounts of TGF β-1 found in normal serum and in serum from patients with peritonitis, an inflammatory disease. The normal amount of TGF β-1 in human serum is approximately 2 nM (39 pG/ml). In patients with peritonitis, the amount increases to nearly 10 nM (169–216 pG/ml). The incorporation of $^3$H-thymidine in the absence of TGF β-1 served as the control. To test the anti-TGF β-1 activity of CITAs, the cells were exposed to 1 nM, 10 nM, and 100 nM CITA-I, CITA-II, and CITA-III in the absence and in the presence of 5.0 nM and 10.0 nM TGF β-1.

Details of Experimental Procedures: $10^4$ MV-1-Lu were plated in each well of a 12 well plate in 2.0 ml minimum essential medium containing non-essential amino acids (MEM) and 10% fetal bovine serum. After 24 hours, the medium was placed with serum free MEM and the cells were further cultured for two hours before the medium was placed with serum free MEM containing the test additives. After exposure to the test medium for 24 hours, the cells were pulse labeled for two hours with 0.5 μCi (methyl-$^3$H)-thymidine, (specific activity 60 Ci/mmol). After pulse labeling, the radioactive medium was removed, and the cells were washed 1× with 10% trichloracetic acid (TCA), 2× with 5% TCA, then 2× with phosphate buffered saline containing 50 μg/ml non-radioactive thymidine. The wash solutions were monitored to establish that no further unbound radioactive thymidine remained. The washed cell layers were dissolved in 1 ml 0.1 N NaOH containing 1% sodium dodecyl sulfate. The radioactivity in the solution was measured in a scintillation counter and expressed as disintegrations per minute (d.p.m.). Each test was carried out in quadruplicate, and the data presented as mean±standard deviation.

Effect of CITAs on DNA Synthesis: CITA-I, CITA-II, and CITA-III decreased DNA synthesis by approximately 20% against the control at all concentrations examined. These observations confirm that the CITAs may bind to TGF β-1 receptors. Each of the three compounds tested markedly reversed the inhibition of DNA synthesis caused by TGF β-1.

Inhibition of TGF β-1 Activity by CITAs: CITA-I, CITA-II, and CITA-III reversed the inhibition of DNA synthesis by TGF β-1. All concentrations of CITAs restored DNA synthesis in MV-1-Lu cells exposed to 5 nM TGF β-1 nearly to the levels seen with the CITAs alone, or 2× the level seen with TGF β-1. All concentration of CITA-I also restored DNA synthesis in cells severely inhibited by 10 nM TGF β-1, resulting in over 10-fold increase in DNA synthesis in the inhibited cells.

Table 1 sets out the inhibition of TGF β-1 activity by CITA-I, Table 2 sets out the inhibition of TGF β-2 activity by CITA-II, and Table 3 sets out the inhibition of TGF β-1 by CITA-III.

TABLE 1

| Additions | 3H-Thymidine Incorporation $10^3$ d.p.m. ± S.D. | (+/−) % change over control with TGF β-1 | (+/−) % change over control when CITA-I is present | % Increase over TGF β-1. TGF β-1 + CITA-I/TGF β-1 × 100 |
|---|---|---|---|---|
| Control (No additions) | 57.71 ± 2.34 | — | — | — |
| +TGF β-1, 5 nM | 16.43 ± 2.95 | −72 | — | — |
| +TGF β-1, 10 nM | 1.91 ± 0.08 | −97 | — | — |
| +CITA-I, 1 nM | 46.46 ± 2.48 | — | −19 | — |
| +CITA-I, 10 nM | 44.93 ± 3.34 | — | −21 | — |
| +CITA-I, 100 nM | 45.10 ± 1.27 | — | −22 | — |
| +TGF β-1, 5 nM + CITA-I, 1 nM | 41.05 ± 2.04 | — | −29 | 250 |
| +TGF β-1, 5 nM + CITA-I, 10 nM | 31.88 ± 2.32 | — | −45 | 194 |
| +TGF β-1, 5 nM + CITA-I, 100 nM | 29.70 ± 2.79 | — | −49 | 181 |
| +TGF β-1, 10 nM + CITA-I, 1 nM | 21.26 ± 1.30 | — | −63 | 1113 |
| +TGF β-1, 10 nM + CITA-I, 10 nM | 26.23 ± 2.73 | — | −55 | 1373 |
| +TGF β-1, 10 nM + CITA-I, 100 nM | 17.30 ± 2.19 | — | −70 | 906 |

TABLE 2

| Additions | 3H-Thymidine Incorporation $10^3$ d.p.m. ± S.D. | (+/−) % change over control with TGF β-1 | (+/−) % change over control when CITA-II is present | % Increase over TGF β-1. TGF β-1 + CITA-II/TGF β-1 × 100 |
|---|---|---|---|---|
| Control (No additions) | 57.71 ± 2.34 | — | — | — |
| +TGF β-1, 5 nM | 16.43 ± 2.95 | −72 | — | — |
| +TGF β-1, 10 nM | 1.91 ± 0.08 | −97 | — | — |
| +CITA-II, 1 nM | 45.10 ± 1.27 | — | −22 | — |
| +CITA-II, 10 nM | 42.03 ± 1.11 | — | −27 | — |
| +CITA-II, 100 nM | 43.08 ± 1.23 | — | −25 | — |
| +TGF β-1, 5 nM + CITA-II, 1 nM | 31.04 ± 1.07 | — | −29 | 184 |
| +TGF β-1, 5 nM + CITA-II, 10 nM | 27.75 ± 1.50 | — | −45 | 169 |
| +TGF β-1, 5 nM + CITA-II, 100 nM | 34.00 ± 0.86 | — | −49 | 207 |
| +TGF β-1, 10 nM + CITA-II, 1 nM | 18.51 ± 1.23 | — | −63 | 970 |
| +TGF β-1, 10 nM + CITA-II, 10 nM | 20.70 ± 2.63 | — | −55 | 1084 |
| +TGF β-1, 10 nM + CITA-II, 100 nM | 18.73 ± 1.67 | — | −70 | 981 |

TABLE 3

| Additions | 3H-Thymidine Incorporation $10^3$ d.p.m. ± S.D. | (+/−) % change over control with TGF β-1 | (+/−) % change over control when CITA-III is present | % Increase over TGF β-1. TGF β-1 + CITA-III/TGF β-1 × 100 |
|---|---|---|---|---|
| Control (No additions) | 57.71 ± 2.34 | — | — | — |
| +TGF β-1, 5 nM | 16.43 ± 2.95 | −72 | — | — |
| +TGF β-1, 10 nM | 1.91 ± 0.08 | −97 | — | — |
| +CITA-III, 1 nM | 44.67 ± 2.26 | — | −23 | — |
| +CITA-III, 10 nM | 47.19 ± 3.00 | — | −18 | — |
| +CITA-III, 100 nM | 44.36 ± 1.76 | — | −23 | — |
| +TGF β-1, 5 nM + CITA-III, 1 nM | 34.00 ± 0.86 | — | −41 | 207 |
| +TGF β-1, 5 nM + CITA-III, 10 nM | 34.03 ± 1.11 | — | −41 | 207 |
| +TGF β-1, 5 nM + CITA-III, 100 nM | 30.23 ± 1.69 | — | −48 | 184 |
| +TGF β-1, 10 nM + CITA-III, 1 nM | 24.36 ± 1.14 | — | −58 | 1275 |
| +TGF β-1, 10 nM + CITA-III, 10 nM | 19.04 ± 1.47 | — | −67 | 997 |
| +TGF β-1, 10 nM + CITA-III, 100 nM | 17.32 ± 0.27 | — | −70 | 907 |

These results confirm that the CITAs are potent inhibitors of TGF β-1 activity.

It is to be understood that while the invention has been described above in conjunction with preferred specific embodiments, the description and examples are intended to illustrate and not limit the scope of the invention, which is defined by the scope of the appended claims.

What is claimed is:

1. A peptide comprising the formula:

$AA_1$-$AA_2$-$AA_3$-Pro-D-Glu-Ala wherein, $AA_1$ is leucine, phenylalanine, α-aminoisobutic acid, N-methylalanine, N-methylisoleucine, or isoleucine;

$AA_2$ is leucine, phenylalanine, α-aminoisobutric acid, N-methylalanine, N-methylisoleucine, or isoleucine; and $AA_3$ is alanine or N-methylalanine.

2. The peptide of claim 1, wherein the peptide comprises the amino acid sequence Leu-Ile-Ala-Pro-D-Glu-Ala.

3. The peptide of claim 1, wherein the peptide comprises the amino acid sequence Phe-Ile-Ala-Pro-D-Glu-Ala.

4. The peptide of claim 1, wherein the peptide comprises the amino acid sequence Leu-Phe-Ala-Pro-D-Glu-Ala.

5. A therapeutic composition, comprsing the formula:

$AA_1$-$AA_2$-$AA_3$-Pro-D-Glu-Ala wherein, $AA_1$ is leucine, phenylalanine, α-aminoisobutric acid, N-methylalanine, N-methylisoleucine, or isoleucine;

$AA_2$ is leucine, phenylalaine, α-aminoisobutric acid, N-methylalanine, N-methylisoleucine, or isoleucine;

$AA_3$ is alaine or N-methylalanine; and, a physiologically acceptable carrier.

6. The composition as in claim 5 wherein the peptide includes Leu-Ile-Ala-Pro-D-Glu-Ala.

7. The composition as in claim 5 wherein the peptide includes Phe-Ile-Ala-Pro-D-Glu-Ala.

8. The composition as in claim 5 wherein the peptide includes Leu-Phe-Ala-Pro-D-Glu-Ala.

9. The composition as in claim 5 wherein the carrier is suitable for topical administration.

10. A method of inhibiting TGF-β activity, comprising:

administering to a patient in need thereof, an effective amount of a peptide specific for inhibiting a fibrotic growth factor, the peptide comprising the formula $AA_1$-$AA_2$-$AA_3$-Pro-D-Glu-Ala wherein, $AA_1$ is leucine, phenylalanine, α-aminoisobutric acid, N-methylalanine, N-methylisoleucine, or isoleucine;

$AA_2$ is leucine, phenylalanine, α-aminoisobutric acid, N-methylalanine, N-methylisoleucine, or isoleucine; and $AA_3$ is alanine or N-methylalanine.

11. The method as in claim 10 wherein the fibrotic growth factor is TGF β-1.

12. The method as in claim 10 wherein the peptide includes Leu-Ile-Ala-Pro-D-Glu-Ala.

13. The method as in claim 10 wherein the peptide includes Phe-Ile-Ala-Pro-D-Glu-Ala.

14. The method as in claim 10 wherein the peptide includes Leu-Phe-Ala-Pro-D-Glu-Ala.

15. The method as in claim 10 wherein the administering is topical application.

16. The method as in claim 15 wherein the peptide is effective to inhibit scar tissue during wound healing.

* * * * *

UNITED STATES PATENT AND TRADEMARK OFFICE
CERTIFICATE OF CORRECTION

PATENT NO.     : 6,509,318 B1
DATED          : January 21, 2003
INVENTOR(S)    : Bhatnagar, Rajendra S. et al.

It is certified that error appears in the above-identified patent and that said Letters Patent is hereby corrected as shown below:

<u>Column 1,</u>
Line 37, please change "tumorigenesis" to -- tumorgenesis --.

<u>Column 3,</u>
Line 63, please change "side-chain" to -- side chain --.

<u>Column 4,</u>
Line 28, please change "syntiesis" to -- synthesis --.
Line 33, please change "sidechain" to -- side chain --.

<u>Column 9,</u>
Line 54, please change "alaine" to -- alanine --.

Signed and Sealed this

Tenth Day of June, 2003

JAMES E. ROGAN
*Director of the United States Patent and Trademark Office*